(12) United States Patent
Pupunat et al.

(10) Patent No.: US 11,420,885 B2
(45) Date of Patent: *Aug. 23, 2022

(54) ELECTROLYSIS METHOD AND DEVICE FOR WATER

(71) Applicant: Waterdiam Group, LLC, Miami, FL (US)

(72) Inventors: Laurent Pupunat, Delémont (CH); Anthony Ginter, Miami, FL (US)

(73) Assignee: Waterdiam Group LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/883,874

(22) Filed: May 26, 2020

(65) Prior Publication Data
US 2020/0283312 A1    Sep. 10, 2020

Related U.S. Application Data

(63) Continuation of application No. PCT/EP2019/053903, filed on Feb. 15, 2019, and a
(Continued)

(51) Int. Cl.
*C02F 1/46* (2006.01)
*C02F 1/00* (2006.01)
(Continued)

(52) U.S. Cl.
CPC .......... *C02F 1/46109* (2013.01); *A61K 35/08* (2013.01); *C02F 1/001* (2013.01);
(Continued)

(58) Field of Classification Search
CPC ...... C02F 1/46109; C02F 1/467; C02F 1/001; C02F 2001/46147; C02F 2209/44;
(Continued)

(56) References Cited

U.S. PATENT DOCUMENTS

| 4,100,052 A | * | 7/1978 | Stillman | ................ C02F 1/4674 |
| | | | | 204/268 |
| 5,399,247 A | * | 3/1995 | Carey | ................. C02F 1/46109 |
| | | | | 204/294 |

(Continued)

FOREIGN PATENT DOCUMENTS

| FR | 2985252 | 7/2013 |
| JP | 6220956 | 10/2017 |

(Continued)

OTHER PUBLICATIONS

Written Opinion issued in PCT Application No. PCT/IB2018/000315 dated May 23, 2018.

(Continued)

*Primary Examiner* — Joseph W Drodge
(74) *Attorney, Agent, or Firm* — CRGO Global; Steven M. Greenberg

(57) ABSTRACT

The invention relates to a easily adaptable or DIY installation water cleaning device on any existing spa or pool, said cleaning device including an electrolysis module equipped with a particular boron-doped diamond electrode on silicon substrate. The inventions also relates to a method to clean water on spa or pools using a water cleaning device comprising said particular boron-doped diamond electrode present on the elecrolysis module. The invention also relates to electrolyzed bathing water for use in the treatment of inflammatory diseases of the skin and for use for use in the treatment of wound healing of the skin.

8 Claims, 4 Drawing Sheets

Related U.S. Application Data continuation of application No. PCT/EP2019/082164, filed on Nov. 21, 2019, and a continuation of application No. PCT/EP2019/082163, filed on Nov. 21, 2019.

(51) Int. Cl.
*A61K 35/08* (2015.01)
*C02F 1/461* (2006.01)
*C02F 1/467* (2006.01)
*C02F 103/42* (2006.01)

(52) U.S. Cl.
CPC .... *C02F 1/467* (2013.01); *C02F 2001/46147* (2013.01); *C02F 2001/46152* (2013.01); *C02F 2103/42* (2013.01); *C02F 2201/4615* (2013.01); *C02F 2201/46145* (2013.01); *C02F 2209/40* (2013.01); *C02F 2209/44* (2013.01)

(58) Field of Classification Search
CPC ........ C02F 2103/42; C02F 2201/46145; C02F 2201/4615; C02F 2209/40; C02F 2201/46152; C02F 1/66; C02F 1/4672; C02F 1/461; C02F 1/46104; C02F 2001/46138; C02F 2001/46133; C02F 2001/46171; C02F 2201/46105; C02F 2201/4611; C02F 2201/46135; C02F 2201/4614; C02F 2201/46175; C02F 2209/06; A61K 35/08; C25B 11/00; C25B 11/02; C25B 11/04; C25B 11/044; C25B 11/059; C25B 11/065; C25B 11/083; E04H 4/12; E04H 4/1209
See application file for complete search history.

(56) References Cited

U.S. PATENT DOCUMENTS

| | | | | |
|---|---|---|---|---|
| 5,900,127 | A * | 5/1999 | Iida | C25B 11/091 204/290.08 |
| 6,375,827 | B1 * | 4/2002 | Kurosu | A61L 2/035 204/263 |
| 2003/0141202 | A1 | 7/2003 | Nakamura et al. | |
| 2005/0023227 | A1 * | 2/2005 | Rychen | C02F 1/4674 210/748.2 |
| 2006/0275498 | A1 | 12/2006 | Bagley | |
| 2008/0105624 | A1 * | 5/2008 | Wormcke | C02F 1/4672 210/748.17 |
| 2008/0223788 | A1 * | 9/2008 | Rimdzius | A61H 33/06 210/664 |
| 2011/0010835 | A1 * | 1/2011 | McCague | C02F 1/4674 4/494 |
| 2011/0024361 | A1 * | 2/2011 | Schwartzel | C02F 1/46109 210/739 |
| 2011/0237484 | A1 * | 9/2011 | Griesbach | D06F 35/003 510/309 |
| 2012/0138478 | A1 * | 6/2012 | Yost, III | C25B 1/13 205/626 |
| 2014/0174942 | A1 * | 6/2014 | Wylie | C25B 15/02 205/342 |
| 2015/0266753 | A1 * | 9/2015 | Fraim | C02F 1/4674 205/759 |
| 2021/0363034 | A1 * | 11/2021 | Ginter | C02F 1/46109 |
| 2021/0403348 | A1 * | 12/2021 | Pupunat | C02F 1/46109 |

FOREIGN PATENT DOCUMENTS

| | | |
|---|---|---|
| WO | 2008029258 | 3/2008 |
| WO | 2008131936 | 11/2008 |
| WO | 2011133148 | 10/2011 |
| WO | 2014015443 | 1/2014 |
| WO | 2017199000 | 11/2017 |

OTHER PUBLICATIONS

International Search Report issued in PCT Application No. PCT/EP2019/053903 dated Apr. 4, 2019.

Preliminary Search Report issued in FR 1871652 dated Oct. 7, 2019.

Preliminary Search Report issued in FR 1871657 dated Oct. 9, 2019.

Julie v. Macpherson, "A practical guide to using boron doped diamond in electrochemical research," Physical Chemistry Chemical Physics, vol. 17, No. 5, Jan. 2015, pp. 2935-2949.

Peter C. Dartsch et al, "DiaClean water technology for the post-harvest preservation of citrus fruits causes no cytotoxic effect after air-drying and storage," Integrative Food, Nutrition and Metabolism, vol. 4, No. 5, Jan. 2015.

Anonymous, "WaterDiam essaie de se passer du chlore pour purifier l'eau des piscines," Jan. 3, 2017, https://www.tracesecritesnews.fr/actualite/waterdiam-89230.

* cited by examiner

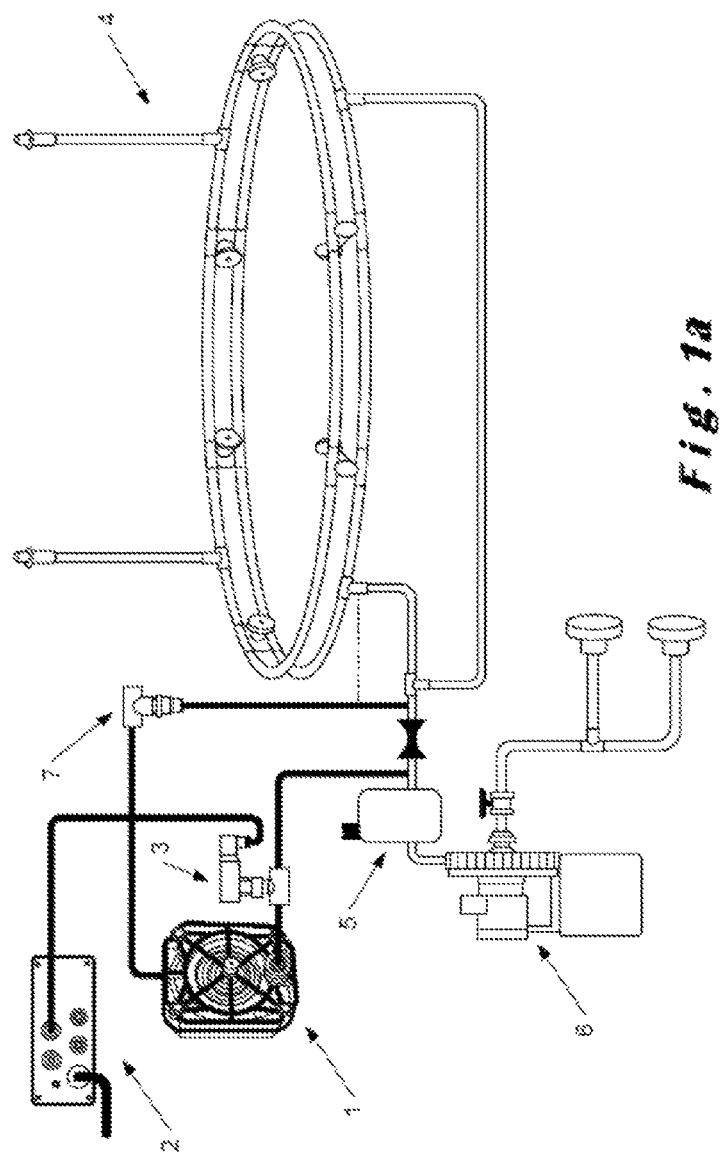

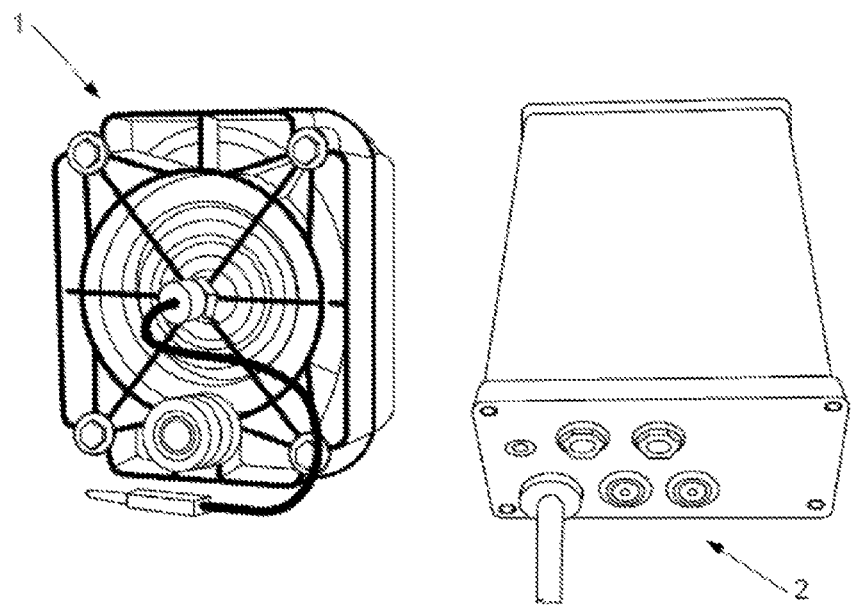
*Fig. 2a*  *Fig. 2b*
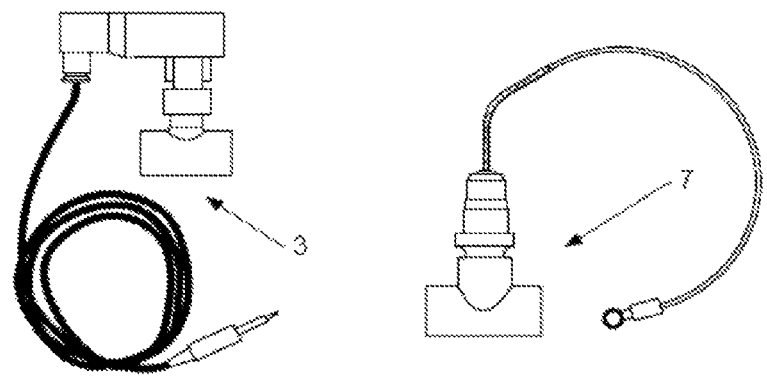
*Fig. 3a*  *Fig. 3b*

ELECTROLYSIS METHOD AND DEVICE FOR WATER

CROSS REFERENCE TO RELATED APPLICATIONS

This application is a continuation "bypass" application of PCT/EP2019/053903 filed Feb. 15, 2019, which claims priority to PCT/IB2018/000315 filed Feb. 28, 2018. This application is also a continuation "bypass" application of PCT/EP2019/082164 filed May 21, 2019, which claims priority to French Application No. FR1871652 filed Nov. 21, 2018. This application is also a continuation "bypass" application of PCT/EP2019/082163 filed May 21, 2019, which claims priority to French Application No. 1871657 filed Nov. 21, 2018. Each of these applications is herein incorporated by reference in their entirety.

FIELD OF THE INVENTION

The invention relates to a device and method used to clean water from spas and pools without fungicidal or biocidal chemical additives. The invention also relates to treating skin conditions using the water obtained from this device and method.

BACKGROUND

Personal or public spas or pools are now commonly present in houses nowadays. Those installation require a minimum of maintenance to work efficiently and to keep the water clean and safe for people using them. The main problem encountered by owners is to be sure that the water is not polluted or comprises bacteria and/or fungus, very often transferred to the water from the skin of the users or contained in the water itself, or by polluted air interfacing with the water.

To solve this issue, regular use of aggressive biocidal and fungicidal chemicals to clean the water is mandatory, especially chlorine derivatives. However such chemicals are not neutral when added to the water and they can be aggressive to bodily tissues and skin. A good example is for instance a burning sensation in the eyes one can feel it when swimming in a public or private pool without glasses.

Chemicals added on the water circuitry of spas or pools require qualified personal to use them, and the chemicals should be handled with care.

Chemical have drawbacks, as they can generate allergies or irritate the skin as well.

For example in US20030141202 it is described a method and apparatus for purging and disinfecting water. The invention discloses the use of an alkaline electrolyte solution that is electrolyzed by a diaphragm-less electrolyzer to provide electrolytic water as purging and disinfecting water. The alkaline electrolyte solution is a mixture of at least one alkaline electrolyte selected from caustic sodium carbonate, caustic potassium carbonate, phosphorous sodium carbonate and sodium hypochlorite, and at least one neutral salt selected from sodium chloride, potassium chloride, sodium bromide and potassium bromide.

The purging and disinfecting water is added to a water circulatory system. The result is that contaminants and noxious chemicals in the circulatory system are oxidation decomposed to thereby purge the circulating water, and noxious microorganisms such as germs, yeasts, fungi, and viruses, growing in the water circulatory system and causing degradation of water or development of slime are disinfected and thereby purged from the water circulatory system. The purging and disinfecting method can be carried out in a simple manner with minimum cost.

Despite the purging and disinfecting method can be carried easily with a minimum of cost, using caustic alkaline compounds is not necessarily safe.

In US2010351604 it is disclosed a method of sanitizing water contained in a spa, which comprises installing a chlorine generating cell including a diamond electrode in a filter compartment of the spa, employing a resin-filled calcium remover bag to reduce the hardness of the water, adding salt to the water; and operating the chlorine generating cell to generate chlorine and other sanitizing agents for sanitizing the water.

Although the method is efficient by using electrolysis it requires addition of salt to the water and a specific installation with a filter compartment which need a certain level of maintenance and specialist to install said device. Based on users testimonies accessible on Internet the use of additional chemicals is always needed to ensure water disinfection.

The drawbacks created by the use of chemicals and the maintenance of such systems, impel to find alternative systems or methods to clean the water used in spas or pools, with a minimum of maintenance need and do not require the use of chemicals which could be over the time harmful to people and do not then offer a real innovative performance.

At the same time, for the treatment of skin conditions, the regular use of chemicals in the form of cream or composition can be irritating over time, moreover regular use can generate resistances or habituations such as treatments with a cortisone base for eczemas. There is a real need to have supporting actions avoiding irritations, or restoring the skin, due to these standard methods. There is also a real need to have alternative methods or compositions that have a non-irritating profile, that make it possible to use as rarely as possible products that can generate resistances or habituations and that make it possible to treat these inflammatory diseases of the skin that are often disabling or trying for the health of patients.

One of the goals of the invention is therefore to overcome the aforementioned disadvantages and to meet the aforementioned needs by providing electrolysed water for use in the treatment of inflammatory diseases of the skin.

In a similar way, although a large therapeutic arsenal exists to care for wounds and to cicatrise them effectively, using chemicals or biological factors is never without risk, as resistance to a composition can set in over the long term. Thus, there is a real need to be able to have new compositions or compounds, making it possible to effectively cicatrise wounds without systematically resorting to complex chemical compounds or biological factors that can sometimes but not always induce rejections or secondary effects that limit or affect the wound healing process.

SUMMARY OF THE INVENTION

In one embodiment, a water cleaning device may include boron-doped diamond electrodes coated on a silicon substrate. This water cleaning device may be used for preparing an electrolyzed water for use in the treatment of inflammatory diseases of the skin, in particular the treatment of eczema or atopic dermatitis. It is also used for preparing an electrolyzed water for use in the treatment of wound healing of the skin.

In addition, the use of such electrodes may allow for intermittent, periodical, electrolysis of the water.

In one embodiment said water cleaning device may be easily adaptable to an existing cleaning system, such as that found in a spa or pool, such that it can be easily fitted into the filtration circuit.

Another aspect of embodiments of the invention is a method to clean bathing water in spas or pools without fungicidal or biocidal chemical additives, which may comprise the steps of:

i) Installing a cleaning device as previously defined in a water filtration circuit of a spa or pool;

ii) Circulating bathing water contained in said spa or pool in said filtration circuit by a filtration system and/or a pump such that said electrodes are in permanent contact with water in said spa or pool filtration circuit, iii) Periodically connecting said electrodes to an electrical power source to periodically electrolyze the water circulated over said electrodes.

In various embodiments, the water may not need to contain any cleaning chemical additives with fungicidal or bacteriocidal effect or the like.

The embodiments may also relate to electrolysed bathing water obtained by the method described above. The embodiments may also relate to electrolysed bathing water according for use in the treatment of inflammatory diseases of the skin. Embodiments may also relate to electrolysed bathing water according to the invention for use in the treatment of wound healing of the skin.

BRIEF DESCRIPTION OF THE DRAWINGS

Features and advantages of the device and method of the invention will become apparent, from the following detailed description of an embodiment of the invention, in reference to the accompanying drawings, among which:

FIG. 1a illustrates an installation set-up for the water cleaning device of the invention in an existing pool having a filtration system;

FIG. 2a shows an electrolysis module comprising two boron-doped diamond electrodes forming parts of the water cleaning device according to the invention;

FIG. 2b shows a power supply module or box;

FIG. 3a illustrates a hydraulic or water flow sensor in connection with an electrolysis module;

FIG. 3b illustrates an earthing apparatus for the water of the spa or pool;

DESCRIPTION OF PREFERRED EMBODIMENTS

Figure 1B:
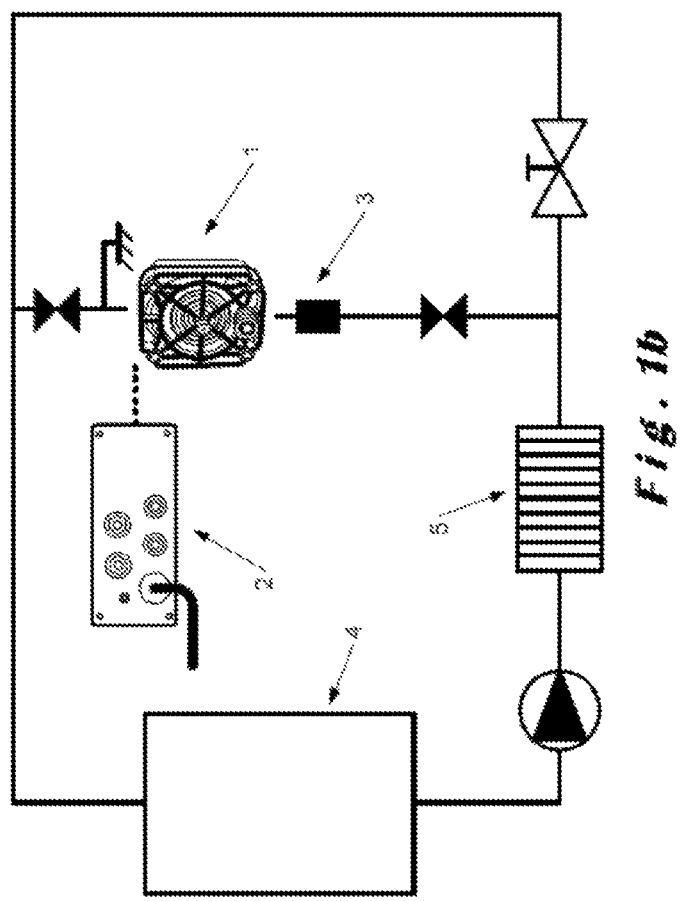
FIG. 1b illustrates inserted corresponding installation set-up in an existing spa system.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

It has been suprisingly found that the drawbacks of the cited prior art are solvent by using a water cleaning device comprising at least two boron-doped diamond electrodes coated on a silicon substrate, in which the concentration of boron is of between 200 ppm (3×1019 B atoms/cm3) and 1500 ppm (2×1020 B atoms/cm3), said diamond electrodes having an active surface area of between about 50 and 100 cm$^2$, preferably between about 60 and 80 cm$^2$, more preferably about 70 cm$^2$. This water cleaning device is used for preparing an electrolyzed bathing water for use in the treatment of inflammatory diseases of the skin, in particular the treatment of eczema or atopic dermatitis. It is also used for preparing an electrolyzed bathing water for use in the treatment of wound healing of the skin.

The inventors have surprisingly discovered that using specific boron-doped diamond electrodes having a surface of more than 50 cm$^2$, with an optimum at about 70 cm$^2$, allows to provide full decontamination of bathing waters without use of chlorinated chemicals or flocculants. This thus allows for more hygienic and dermatologically neutral water cleaning in spas and pools.

In addition, the use of such electrodes allows for intermittent, periodical, electrolysis of the water, which is more efficient from an electrical power consumption point of view.

In preferred embodiment said water cleaning device is easily adaptable to an existing cleaning system of a spa or pool, such that it can be easily fitted into the filtration circuit without fuss or amendment works for users.

The operating voltage of the electrodes present in the water cleaning device is comprised between −1V and −2V on cathodic polarization and between +2V and +4V on anodic polarization.

The electrodes of the water cleaning devices can adopt various shapes such as a circular, square, triangular rectangular or star-shaped transversal cross-section in a plane perpendicular to a longitudinal direction of said electrode.

In a preferred embodiment the thickness of the boron doped diamond layer is comprised between 1 μm and 9 μm, preferably 1 and 4 μm, more preferably 1 and 3 μm.

The resistivity of the silicon substrate in the water cleaning device is comprised between 50 to 200 mOhm·cm, preferably 50 to 150 mOhm·cm.

In a preferred embodiment said water cleaning device according to any of the hydraulic or water flow sensor.

Another aspect of the invention is a method to clean bathing water in spas or pools without fungicidal or biocidal chemical additives, which comprises the steps of:

iv) Installing a cleaning device as previously defined in a water filtration circuit of a spa or pool;

v) Circulating bathing water contained in said spa or pool in said filtration circuit by a filtration system and/or a pump such that said electrodes are in permanent contact with water in said spa or pool filtration circuit, vi) Periodically connecting said electrodes to an electrical power source to periodically electrolyze the water circulated over said electrodes.

In the context of the present invention, the terms "periodical" or "periodically" in relation to the connection of the electrodes to electrical power and to the electrolysis cycles thereby delivered on the water circulated in the filtration circuit of a spa or pool shall be construed as meaning "non-permanent", i.e. intermittent, occurring at time-spaced intervals, said time-spaced intervals not necessarily being constant over time.

In other words, the terms "periodical" or "periodically" shall not be interpreted in such a way that they are strictly limited to a mathematical definition of those terms, i.e. periods of identical duration cyclically repeating over time.

In a preferred embodiment when applying the method of clean bathing according to the invention is to maintain the pH of the water present in said spas or pools between 6 and 8.

In the method according to the invention is it important that the temperature of the water is maintained between 35° C. and 45° C.

In the method according to the invention the water is circulated continuously in said filtration circuit and the electrodes are periodically powered to perform electrolysis cycles of at least 30 min to one hour.

In a preferred embodiment of the method according to the invention the electrode are powered at regular intervals.

In a preferred embodiment of the method according to the invention 4 to 12 electrolysis cycles are conducted per 24 h, i.e. the electrodes are electrically powered 4 to 12 times a day. Preferably, two consecutive electrolysis cycles shall not be completed within less than 2 h, to maintain full efficiency of the water cleaning method over time, in particular over months, without requiring changing the bathing water.

In the method according to the present invention, the water does need, and should preferably not contain any cleaning chemical additives with fungicidal or bacteriocidal effect or the like. The only acceptable additive to allow proper performance of the invention may be a conductivity salt such as NaCl to improve electrolysis cycles. Said conductivity salt may be present at a concentration of 0.2 to 2 g per Liter, preferably from 0.5 to 1 g per Liter.

The invention also relates to electrolysed bathing water obtained by the method described above.

The invention also relates to electrolysed bathing water according to the invention for use in the treatment of inflammatory diseases of the skin.

The invention also relates to electrolysed bathing water according to the invention for use in the treatment of wound healing of the skin.

The electrolysed bathing water according to the invention for use in the treatment of inflammatory diseases of the skin or for wound healing is used over a period ranging from 5 to 60 minutes of exposure.

The electrolysed bathing water is obtained by means of the water cleaning device that allows for the implementation of the method described above, said cleaning device being where applicable present in a fixed or movable manner in a swimming pool, a spa, a bathtub or a shower. It can also be present in a traditional water distribution circuit, preferably at the distribution outlet such as a tap.

With reference now to the drawings, FIGS. 1a and 1b show the benefit of a water cleaning device according to the present invention.

From an existing spa 4 or pool system with its own water circuit 4', it is very easy to adapt a water cleaning device according to the invention, comprising a power supply module or box 2 in connection with at least one electrolysis module 1, which comprises at least two boron-doped diamond electrode deposited on a silicon substrate. The water cleaning device also comprises a hydraulic or water flow sensor 3 shown in FIG. 3a in connection with the electrolysis module and an earthing apparatus 7 (shown in FIG. 3b) to electrically connect the water of the spa or pool to the ground directly before or after the water has been circulated in the electrolysis module 1.

One advantage of the present invention is that the water cleaning device proposed is made of simple and inexpensive elements easy to adapt and install in existing spa or pool systems.

As highlighted in FIGS. 1a and 1b, the water cleaning device of the invention may be connected to an existing spa 4 or pool system 4'. Said spa 4 or pool system 4' usually comprises water pipes or tubes forming a hydraulic circuit for circulating the water of said spa or spool in a closed loop.

As represented in FIGS. 1a and 1b, such existing spa 4 or pool system 4' further comprises a filtration system 6 and a heater 5 integrated in the hydraulic circuit in order to periodically or permanently filter and the water and keep it at the correct temperature. Said filtration system 6 extracts the dust and the biological material present or generated in the water through normal usage of the spa or the pool.

These classical systems usually require usage of chemical compounds such as chlorine as cleaning and purifying agents in the water on a regular basis, for example in pill, liquid or powder form, to remove or destroy fungus or bacteria present in water. Other known chemicals such as Trichloro isocyanure or PHMB for polyhexamethyleme biguanide can be used as well.

Adding such chemicals can be detrimental to the safety and comfort of users as, despite the presence of a filtering system, they can cause allergies or skin and tissues irritation of users.

The water cleaning system according to the invention advantageously allow for effective cleaning and cleaning of the water of spas and pools without using any chlorinated additives or fungicides, thanks to electrolysis of the water of a spa or pool by means of boron-doped diamond electrodes, which produces into the water natural disinfecting agents, including active oxygen, and eliminates micro-organisms, fungi, urea and like faster than any chlorinated additive.

This provides an undeniable advantage over the use of chemical compounds to clean the water of spa or pool. The only requirement for the cleaning system and method of the invention to work effectively is the presence in the water of a spa or pool to be disinfected of conductivity salts such as NaCl, either naturally present or added in the water if required. Said conductivity salt is present at the concentration of 0.2 to 2 g per Liter, preferably from 0.5 to 1 g per Liter, which is probably the lowest content of NaCl or conductivity salt usually present on spa and pools. By avoiding any added chemical compounds, the drawbacks such as skin or eyes irritation disappear for users.

The working principles of the water cleaning device of the invention, which will be described further, allows for a long period of time (about 3 months) to keep the water clean in said spa and pool without changing it and therefore reduces the maintenance of the spa or pool (changing the water, draining the spa or spool, changing the filter . . . ).

In the water cleaning device of the invention there is at least one electrolysis module 1 comprising at least two boron-doped diamond electrodes coated on a substrate.

Said electrode(s) provides a contact area that is comprised between 50 and 100 $cm^2$, preferably 60 and 80, more preferably about 70 $cm^2$.

Said surface area as well as the diamond nature of the electrode(s) provides a double advantage over the existing spa or pool cleaning systems configurations found in the prior art.

The first advantage with said surface area of the electrode(s) is that the contact between the electrode and the water to be treated is optimal, thus said contact area allows to treat efficiently about 6 to 10 $m^3$ of water per day with a reduced consumption of electricity during the cleaning process.

A second important advantage is the operating windows (meaning the electrical parameters for the power supply of the electrode(s)) of said particular boron-doped diamond electrode(s).

Figure 4:
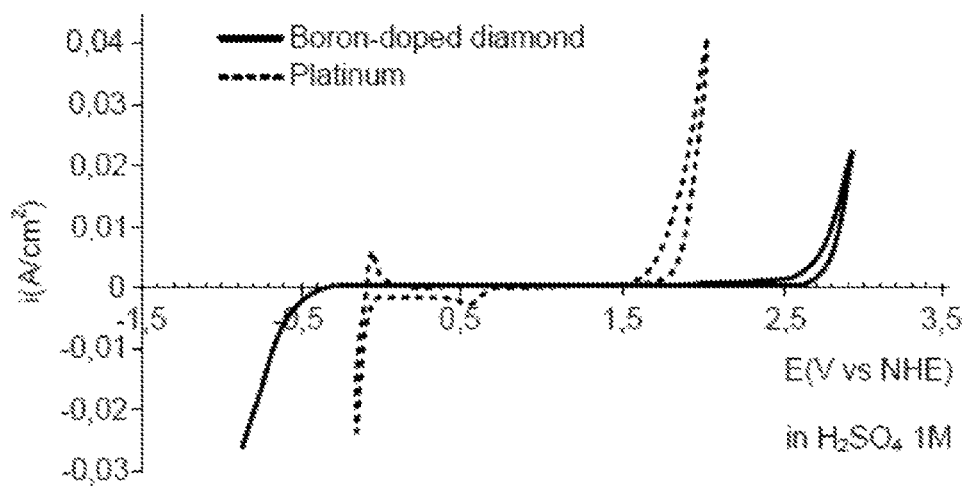
FIG. 4 illustrates the operating windows comparison between a boron-doped diamond electrode vs a platinum electrode, where the abscissa representing the voltage vs NHE (normal hydrogen electrode) and the ordinate the intensity (A/cm$^2$) in $H_2SO_4$ 1M.

This aspect of the electrode(s) is very important as highlighted in FIG. 4 when comparing a classical platinum electrode used for electrolysis purpose with the one used in the cleaning device according to the invention.

The comparison of FIG. 4 shows that the particular diamond electrode of the water cleaning system of the invention, with its specific surface area, allows to work within a higher voltage window than the one of platinum.

The boron doping of the diamond electrode also has its importance on the properties of the water obtained; the concentration of boron is between 200 ppm ($3\times10^{19}$ B atoms/cm$^3$) and 1500 ppm ($2\times10^{20}$ B atoms/cm$^3$).

This boron concentration as well as the nature of the electrodes with a diamond base on silicon provide it with properties that allow it to operate on a potential between −1V and −2V on the cathode polarisation and on +2V and +4V on the anode polarisation. It is very important as highlighted in FIG. 4 that the electrode according to the present invention is efficient when operating on a potential comprised between −1V and −2V on cathodic polarization and +2V and +4V on anodic polarization; in comparison the platinum electrode is only operable efficiently between −0.3V on cathodic polarization and a maximum of +1.7V on anodic polarization.

This larger working window is of importance as shown in FIG. 4, because it has a direct impact on the electrolysis of the water according to the method of the invention.

Without being limited by theory, accessing operating overvoltages that are much higher than the conventional and expensive electrodes which are platinum electrodes, makes it possible to obtain water that has an interesting therapeutic potential on diseases of the skin. The physical-chemical interaction between the electrodes used for the invention and the molecules of electrolysed water allows for a functionalisation of the water that is not easy to characterise with current techniques but of which the therapeutic effects on the skin can be observed directly. These boron-doped diamond electrodes make it possible to generate or to activate ionic and radical species that will provide the water with a therapeutic potential and more particularly on the processes of wound healing and inflammation. The water produced by the method of the invention has therapeutical and biological properties and shows activity that is undeniable with regards to conventional non-electrolysed water according to the method of the invention.

While with platinum electrode we could have valuable chemical compounds generated to clean correctly when there is chemical additive added to the water generated such as $O_3$ from $H_2O$ or $O_2$ from $H_2O$ or $Cl_2$ from $Cl^−$, the use of the electrode according to the present invention does no longer require any additives. Without being bonded by theory, it seems that using said particular electrodes makes the water is own cleaning agent.

Therefore said particular diamond electrode(s) of the water cleaning system of the invention totally avoids the use of chemicals commonly used in spas or pools to clean them and is efficiently treating a large volume of water for a long period of time.

The boron-doped diamond electrode(s) could be according to the prior art deposited on various substrates such as metal or alloys, but the most convenient substrate found to be suitable for the application contemplated on spa or pool is a silicon substrate.

The thickness of said silicon substrate where the boron doped diamond layer is deposited on is about 1 μm and 9 μm, preferably 1 and 4 μm, preferably 1 and 3 μm.

Silicon is also preferred as a substrate for supporting the boron doped diamond layer as it cannot rust into water and a strong and efficient bond between silicon and the boron doped diamond layer can be obtained upon formation of the electrode(s).

The boron doped diamond layer is for example deposited by Chemical vapor deposition also known as CVD or by plasma assisted chemical vapor deposition process PACVD. Other examples of process for example, hot filament CVD (HFCVD); combustion flame CVD (CFCVD); arc jet plasma-assisted CVD (AJCVD); laser-assisted CVD (LCVD); and RF or microwave plasma-assisted CVD (RF or MW CVD) could be also contemplated.

The boron-doped diamond electrode(s) in the electrolysis module 1 of the cleaning system of the invention may have various shapes, and for example show a circular, square, triangular rectangular or star-shaped transversal cross-section in a plane perpendicular to a longitudinal direction of said electrode(s).

The electrolysis module 1 is open to a hydraulic or water flow in the water circuit of a spa or pool and connected to the electric power supply module 2. To work properly and not jeopardize the proper working conditions, the electrode(s) are supplied a direct current from the power supply module 2 as show in FIG. 2b. The power supply 2 is connected with the electrolysis module 1 providing a direct current to said electrode, generally the latter is set between 1.5 A and 3 A, usually at 2.5 A. In case of required inversion of polarity such can be done automatically by the power supply module 2.

To work properly the electrolysis module 1 requires to be permanently bathed into water, and preferably that water is circulated over the electrodes by the filtration system 6 of the spa or pool. As shown in FIG. 3a a hydraulic or water flow sensor is preferably added in the water cleaning system shortly before a water inlet or after an outlet of the electrolysis module 1, that will measure the water flow passing there through.

According to FIGS. 1a and b, the electrolysis module 1 is connected in the existing water circuitry of the spa or pool via O-rings at least one inlet and at least one outlet of the electrolysis module 1. The water flow sensor is in connection with the power supply module 2, and if no water is flowing in the circuit, then the power supply module 2 shuts power supply to the electrolysis module 1.

Should the electrode(s) in the electrolysis module 1 not be bathed into water, then the power supply module 2 also detects the opening of the electrical circuit and thus shuts down power as well.

The water cleaning device according to the invention further comprises an earthing apparatus 7 (shown in FIG. 1a and FIG. 3b), for example in a T shaped electrode or else, configured to connect the water of the spa or pool system to ground, to avoid that any electrical short-circuit in the electrolysis module 1 or power supply module 2 may harm users present in the spa or pool.

The water cleaning device according to the present invention can advantageously work in an automatic mode or can be activated or deactivated on demand, manually or by using a remote controller system.

Another advantage of the present invention lies in the fact that the water cleaning device does not necessarily need permanent activation but can be activated periodically, i.e. at timely intervals, preferably but not necessarily regular intervals. It has been found that electrolyzing the water at regular intervals allows for the water to remain clean for a long period of time. Activating the electrolysis module between 4 to 12 times for at least one hour per day is sufficient to obtain clean water, for over 3 month to one year. In case of strong frequentation, the electrolysis module can be activated full time for up to one full day.

Another object of the present invention is a method to clean bathing water in spas or pools without fungicidal or biocidal chemical additives, wherein the method comprises the steps of:

Installing a water cleaning device according as described previously in an existing water filtration circuit of a spa or pool;

Circulating bathing water contained in said spa or pool in said filtration circuit by a filtration system and/or a pump such that the boron-doped diamond on silicon substrate electrodes present in the electrolysis module 1 are in permanent contact with water in said spa or pool filtration circuit;

and then periodically applying an electric current to said electrode to electrolyze the water circulating over said electrodes.

The water cleaning device subjects the water passing through the electrolysis module to a quantity of current during the electrolysis process between 15 and 500 mAh/L of water, more preferably 40 to 250 mAh/L of water, even more preferably 50 to 200 mAh/L, the electrolysis duration being between 15 and 60 minutes per cycle, 4 to 12 cycles per day.

As mentioned previously to enhance the capacity of the system to speed the water cleaning process or to treat efficiently a higher volume of water, it is possible to use at least one electrolysis module, just requiring to adapt accordingly the connection of the existing water circuit with the electrolysis module present with the water cleaning device.

It is important that the pH of the water should not be too much acid to promote water comfort, the ideal pH to use efficiently the water cleaning device is between 6 and 8.

It is also important to avoid having warm water on the cleaning device system; water maintained between 35° C. and 45° C., ideally 40° C. is the best temperature for using the water cleaning device.

Another advantage of the cleaning device according to the invention is the low level of maintenance on the electrodes present in the electrolysis module 1. A simple inversion of the polarity of said boron doped diamond electrodes will be required to clean them and is performed by the electronic card of the dedicated box.

By way of comparative example, the inventors tested two electrolysis protocols, which demonstrate the efficiency of the periodical electrolysis process of the invention in the cleaning of water contained in a spa.

More specifically, electrolysing the spa water once a day during 12 continuous hours applying a current charge of 10 to 12 Ah/day·m$^3$ does not allow keeping spa water sanitized for use of 4 persons/week over a 1 month period, while the filtration of the water is continuously activated.

By opposition, conducting electrolysis cycles of the water for between 30 min and 1 h applying a current charge of 10 to 12 Ah/day·m$^3$, at regular intervals between 4 to 12 times a day over a 1 month period, while the filtration of the water is continuously activated, provides a perfectly sanitized spa water with no use of any chemical nor any water replacement.

In addition, use of standard salt electrodes instead of boron-doped diamond electrodes according to the current invention induces a strong increase in concentration of combined chlorinated compounds (chloramines) in the water, which is totally absent with the current invention system and diamond electrodes.

Regarding the skin conditions and the wound healing, the present invention relates to a particular electrolysed bathing water obtained by said described method that makes use of particular boron-doped diamond electrodes fixed on silicon making it possible to resolve the aforementioned problems or disadvantages. It has the following advantages and improvements:

It is not based on conventional drugs which over prolonged use cause, due to the nature of the disease (its recurrence), a habituation or a resistance, It is hardly or not at all invasive, The water is unlimited and easily accessible, It does not require the delivery of a prescription or particular precautions when it is used, The cost of production thereof is relatively low, The possibility of easily "reactivating" the water in an active or therapeutic state substantially limits its expiry date, The absence of allergies or habituation.

The bathing water as a product obtained by the electrolysis/cleaning method of the invention is able to be used in the treatment of inflammatory diseases of the skin and more particularly for use in the treatment of eczema or atopic dermatitis. This bathing water also has cicatrising properties, and is able to be used in the treatment of the wound healing or of associated disorders. The bathing water thus obtained can be used within different devices. The devices used can be selected among a swimming pool, a spa, a bathtub or a water distribution system such as a tap or a shower or a suitable ambulatory treatment device. The electrolysis module used will then be integrated into an existing water circuit so as to prepare the electrolysed water, for example in swimming pools or spas, or added and connected as a mobile device on a hydraulic circuit linked to a tap if a shower or a bathtub is considered. In the context of an ambulatory treatment device, an electrolysis device and a reservoir of water with a determined volume can be connected or assembled in a closed circuit with an applicator tap or member, with a recovery device also able to be associated in such a way as to prevent losses in the drain of electrolysed treatment water and the recycling thereof to the reservoir for another electrolysis.

The nomad or mobile or even fixed mode of usage and the adaptability thereof to existing devices so as to produce electrolysed water useful in the treatment of inflammatory diseases of the skin is an advantage of the present invention.

The initial water subjected to the electrolysis, regardless of the source thereof, is cleaned and potentialised by the electrolysis. It is therefore not necessary to use distilled water, as the method of electrolysis of the invention provides a natural anti-bacterial and anti-fungal effect, which makes it possible to obtain high quality water.

Any water, whether it is natural, spring water or from the mains can be used in the method of producing electrolysed water according to the invention. The advantage and the flexibility of use of the electrolysis module according to the invention makes it possible to obtain from a common water source a treatment that is less expensive because it does not require any conventional chemicals in the treatment of inflammatory diseases of the skin or in the treatment of the cicatrisation or of associated disorders, while still avoiding the secondary effects of said chemicals.

In the case of use in devices such as swimming pools, spas, bathtubs, etc. . . . the advantage is that a large surface can be treated; it can concern the entire body or all or a part of the body, and is especially effective when the inflammatory disease is localised in different zones; this avoids using substantial quantities of cream.

The treatment can take place in a bath for a duration of exposure ranging from 5 to 45 minutes and repeated more than once a day, for example until the inflammatory symptoms disappear or are attenuated, or until the cicatrisation occurs.

In the case of treating a child suffering from severe eczema on the upper and lower limbs and the back, the treatment is more effective after two days and as soon as 5 hours after exposure for fifteen minutes in a bath comprising the electrolysed water according to the method of the invention. Before being placed in the bath containing the water, a very high density of inflammation of the skin is observed on the foot, which is attenuated 5 hours after exposure in the bath; then, two days after the bath, the inflammatory portion seems to be in the form of a scab that is still reddish but no longer causes any itching conducive to forming scabs that will subside afterwards.

Those skilled in the art will appreciate from the foregoing that various adaptations and modifications of the just described embodiments can be configured without departing from the scope and sprit of the invention. Therefore, it is to be understood that, within the scope of the appended claims, the invention may be practiced other than as specifically described herein.

The invention claimed is:

1. A method to purify bathing water in a spa or a pool without fungicidal additives and without biocidal chemical additives, the method comprising the steps of:
   i) Installing a water purification device in series with a water filtration circuit of a spa or pool, said water purification device comprising two boron-doped diamond electrodes coated on a silicon substrate, in which the concentration of boron is between 200 ppm and 1500 ppm, said diamond electrodes corresponding respectively to an anode and a cathode, each having an active surface area between 50 and 100 cm2, wherein the operating voltage of said electrodes is between −1V and −2V on cathodic polarization and between +2V and +4V on anodic polarization, wherein the device is configured to allow, in use, permanent circulation past the electrodes in a closed loop;
   ii) Circulating said bathing water contained in said spa or pool in said filtration circuit by a filtration system and/or a pump such that said electrodes are in permanent contact with water in said spa or pool filtration circuit; and
   iii) Periodically connecting said electrodes to an electrical power source to periodically electrolyze the water circulated over said electrodes.

2. The method according to claim 1, wherein the pH being present in the spa or pool is maintained at between 6 and 8.

3. The method according to claim 1, wherein the temperature of the water in the spa or pool is maintained at between 35° C. and 45° C.

4. The method according to claim 1, wherein the water is circulated continuously in said filtration circuit and the electrodes are periodically powered to perform electrolysis cycles of 30 min to one hour.

5. The method according to claim 1, wherein the periodically connecting said electrodes occurs in 4 to 12 electrolysis cycles per 24 hours.

6. The method according to claim 1, wherein the water purification device subjects the water passing through the electrodes to a quantity of current during the electrolysis process of between 15 and 500 mAh/L of water.

7. The method according to claim 1, wherein the water purification device subjects the water passing through the electrodes to a quantity of current during the electrolysis process of between 40 and 250 mAh/L of water.

8. The method according to claim 1, wherein the water purification device subjects the water passing through the electrodes to a quantity of current during the electrolysis process of between 50 and 200 mAh/L of water.

* * * * *